US00PP34825P2

(12) United States Plant Patent
Lazzeri

(10) Patent No.: US PP34,825 P2
(45) Date of Patent: Dec. 13, 2022

(54) ***MANDEVILLA* PLANT NAMED 'LVDIP1807'**

(50) Latin Name: *Mandevilla hybrida*
Varietal Denomination: 'LVDIP1807'

(71) Applicant: Carlo Lazzeri, Vacaria (BR)

(72) Inventor: Carlo Lazzeri, Vacaria (BR)

( * ) Notice: Subject to any disclaimer, the term of this patent is extended or adjusted under 35 U.S.C. 154(b) by 0 days.

(21) Appl. No.: 17/829,285

(22) Filed: May 31, 2022

Related U.S. Application Data

(60) Provisional application No. 63/197,795, filed on Jun. 7, 2021.

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Mandevilla* plant named 'LVDIP1807', characterized by its relatively compact, upright to outwardly spreading plant habit; moderately vigorous to vigorous growth habit; early and freely flowering habit; single bright pink-colored flowers; and good container performance.

2 Drawing Sheets

Figure 1:
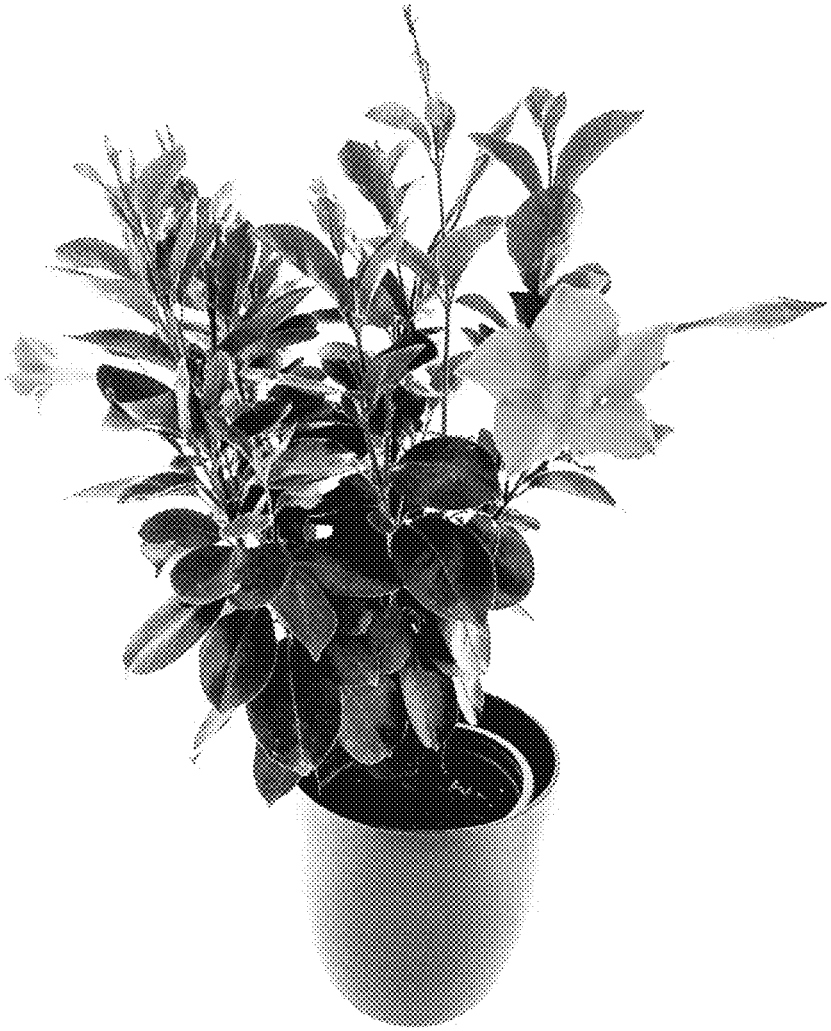

Botanical designation: *Mandevilla hybrida.*
Cultivar denomination: 'LVDIP1807'.

STATEMENT REGARDING PRIOR DISCLOSURES BY INVENTOR/APPLICANT

An European Plant Breeder's Rights application for the instant plant was filed by the Inventor/Applicant on Jun. 7, 2021, application number 2021/1466. Foreign priority is not claimed to this application.

BACKGROUND OF THE INVENTION

The present invention relates to a new and distinct cultivar of *Mandevilla* plant, botanically known as *Mandevilla hybrida* and hereinafter referred to by the name 'LVDIP1807'.

The new *Mandevilla* plant is a product of a planned breeding program conducted by the Inventor in Vacaria, Brazil. The objective of the breeding program is to develop new strong and freely flowering *Mandevilla* plants with attractive flowers and good garden performance.

The new *Mandevilla* plant originated from a cross-pollination in 2017 in Vacaria, Brazil of *Mandevilla hybrida* 'Fisrix Pinka' (trade name, Rio Pink), disclosed in U.S. Plant Pat. No. 20,644, as the female, or seed, parent with *Mandevilla hybrida* 'Amore Mio', not patented, as the male, or pollen, parent. The new *Mandevilla* plant was discovered and selected by the Inventor as a single flowering plant from within the progeny of the stated cross-pollination grown in a controlled greenhouse environment in Vacaria, Brazil in November, 2018.

Asexual reproduction of the new *Mandevilla* plant by terminal stem cuttings in a controlled environment in Vacaria, Brazil since January, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LVDIP1807'. These characteristics in combination distinguish 'LVDIP1807' as a new and distinct *Mandevilla* plant:

1. Relatively compact, upright to outwardly spreading plant habit.
2. Moderately vigorous to vigorous growth habit.
3. Early and freely flowering habit.
4. Single bright pink-colored flowers.
5. Good container performance.

Plants of the new *Mandevilla* can be compared to plants of the female parent, 'Fisrix Pinka'. Plants of the new *Mandevilla* differ primarily from plants of 'Fisrix Pinka' in the following characteristics:

1. Plants of the new *Mandevilla* are not as vigorous as plants of 'Fisrix Pinka'.
2. Plants of the new *Mandevilla* have smaller flowers than plants of 'Fisrix Pinka'.
3. Plants of the new *Mandevilla* have darker pink-colored flowers than plants of 'Fisrix Pinka'.

Plants of the new *Mandevilla* can be compared to plants of the male parent, 'Amore Mio'. Plants of the new *Mandevilla* differ primarily from plants of 'Amore Mio' in the following characteristics:

1. Plants of the new *Mandevilla* have darker green-colored leaves than plants of 'Amore Mio'.

2. Plants of the new *Mandevilla* have darker pink-colored flowers than plants of 'Amore Mio'.

Plants of the new *Mandevilla* can also be compared to plants of *Mandevilla hybrida* 'Sunpararosta', disclosed in U.S. Plant Pat. No. 23,213. In side-by-side comparisons, plants of the new *Mandevilla* differ primarily from plants 'Sunpararosta' in the following characteristics:

1. Plants of the new *Mandevilla* are more upright than and not as trailing as plants of 'Sunpararosta'.
2. Plants of the new *Mandevilla* are not as vigorous as plants of 'Sunpararosta'.
3. Plants of the new *Mandevilla* have darker pink-colored flowers than plants of 'Sunpararosta'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'LVDIP1807' grown in a container.

Figure 2:
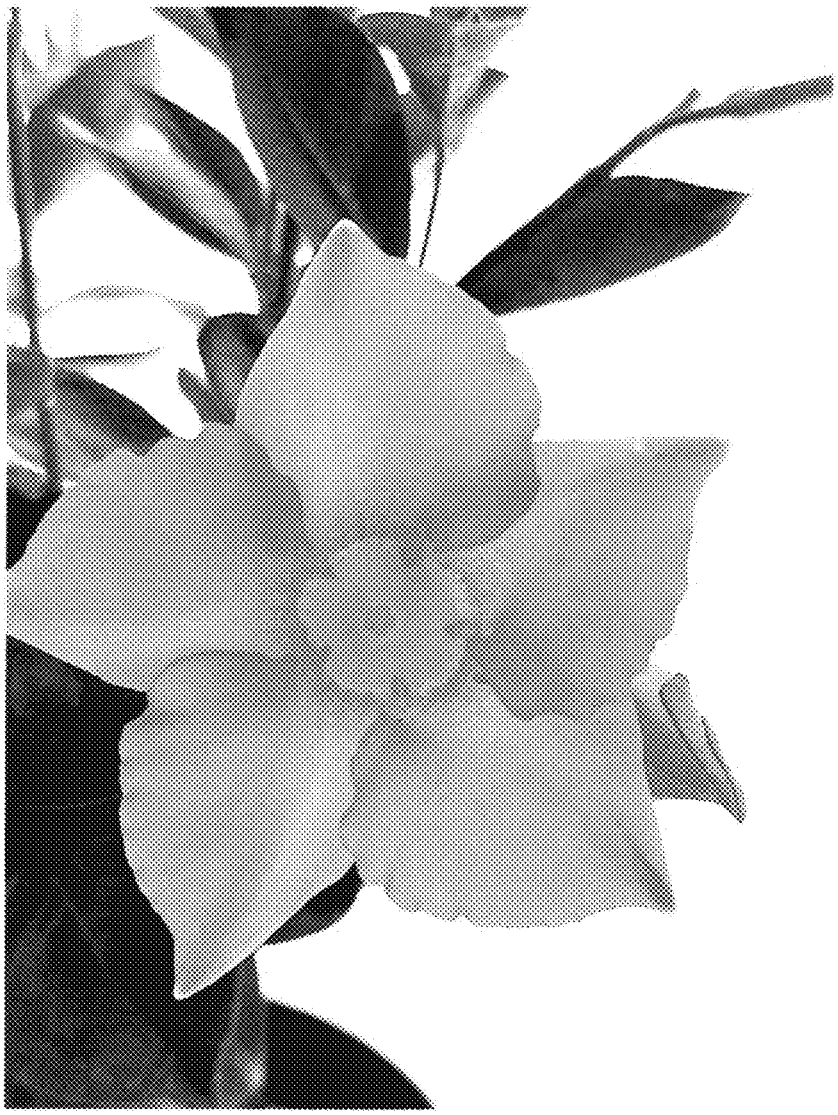

The photograph on the second sheet (FIG. 2) is a close-up view of a typical flower of 'LVDIP1807'.

DETAILED BOTANICAL DESCRIPTION

The aforementioned photographs and following observations, measurements and values describe plants grown during the summer in 10.5-cm containers in a polyethylene-covered greenhouse in Merano, Italy and under cultural practices typical of commercial *Mandevilla* production. During the production of the plants, day temperatures ranged from 20° C. to 28° C. and night temperatures ranged from 10° C. to 18° C. Plants were 20 weeks old when the photographs and description were taken. In the following description, color references are made to The Royal Horticultural Society Colour Chart, 2015 Edition, except where general terms of ordinary dictionary significance are used.

Botanical classification: *Mandevilla hybrida* 'LVDIP1807'.

Parentage:

*Female, or seed, parent.*—*Mandevilla hybrida* 'Fisrix Pinka', disclosed in U.S. Plant Pat. No. 20,644.

*Male, or pollen, parent.*—*Mandevilla hybrida* 'Amore Mio', not patented.

Propagation:

*Type*.—By vegetative cuttings.

*Time to initiate roots, summer*.—About three weeks at temperatures about 25° C.

*Time to initiate roots, winter*.—About four weeks at temperatures about 14° C.

*Time to produce a rooted young plant, summer*.—About five weeks at temperatures about 25° C.

*Time to produce a rooted young plant, winter*.—About six weeks at temperature about 14° C.

*Root description*.—Thin, fibrous; typically creamy white in color, actual color of the roots is dependent on substrate composition, water quality, fertilizers, substrate temperature and physiological age of roots.

*Rooting habit*.—Freely branching; medium density.

Plant description:

*Plant and growth habit*.—Relatively compact, upright to outwardly spreading plant habit; roughly obovate to broadly obovate in overall shape; moderately vigorous to vigorous growth habit and moderate growth rate.

*Plant height, soil level to top of foliar plane*.—About 40.2 cm.

*Plant height, soil level to top of floral plane*.—About 39.4 cm.

*Plant diameter* (*spread*).—About 34.7 cm.

*Lateral branch description*.—Branching habit: Freely branching habit, typically about four primary lateral branches each with about three secondary lateral branches. Length: About 14.7 cm. Diameter: About 2.25 mm. Internode length: About 3.5 cm. Aspect: Primary lateral branches, mostly upright; secondary lateral branches, about 20° to 30° from primary branch axis. Strength: Strong. Texture and luster: Smooth, glabrous; slightly glossy; becoming woody with development. Color, developing: Close to 144B. Color, developed: Close to 144A; when woody, close to N199A, N199B and 200A to 200C.

Leaf description:

*Arrangement*.—Opposite or in whorls of three, simple.

*Length*.—About 6.6 cm.

*Width*.—About 4.3 cm.

*Shape*.—Broadly ovate to broadly obovate.

*Apex*.—Apiculate to abruptly acute.

*Base*.—Truncate to rounded.

*Margin*.—Entire.

*Texture and luster, upper and lower surfaces*.—Smooth, glabrous; moderately coriaceous; moderately glossy.

*Venation pattern*.—Pinnate.

*Color*.—Developing leaves, upper surface: Close to 144A. Developing leaves, lower surface: Close to 146D moderately tinged with close to 174A. Full expanded leaves, upper surface: Darker than 139A; venation, close to 143C. Fully expanded leaves, lower surface: Close to 146A; venation, close to a blend of 145A and 145B.

*Petioles*.—Length: About 9 mm. Diameter: About 1.75 mm by 1.75 mm. Strength: Moderately strong. Texture and luster, upper and lower surfaces: Smooth, glabrous; slightly glossy. Color, upper surface: Close to 144A; margins, close to 146B. Color, lower surface: Close to 145B; proximally, close to 144A.

Flower description:

*Flower type and flowering habit*.—Single salverform flowers arranged in terminal and axillary cymes; flowers face outwardly to slightly upright and slightly nodding; freely flowering habit with about five flowers per inflorescence and about 85 flower buds and open flowers developing per plant during the flowering season.

*Natural flowering season*.—Plants flower continuously from spring into the autumn in Italy; plants begin flowering about 45 days after planting rooted young plants.

*Flower longevity on the plant*.—Individual flowers last about ten days; flowers not persistent.

*Fragrance*.—None detected.

*Inflorescence height*.—About 13.6 cm.

*Inflorescence diameter*.—About 10.3 cm.

*Flower buds*.—Length: About 5.7 cm. Diameter: About 1 cm. Shape: Narrowly oblanceolate. Texture and luster: Smooth, glabrous; slightly glossy. Color: Distally, close to a blend of 53C and 58A; mid-section, close to 48A to 48B with venation, close to 145C; proximally, close to 145B and tube, close to 145A slightly tinged with close to 172C.

*Flowers*.—Appearance: Flared trumpet, corolla fused and five-parted. Diameter: About 7.2 cm by 7.2 cm. Depth (length): About 6.5 cm. Throat diameter: About 1.5 cm. Tube length: About 4.7 cm. Tube diameter: Proximally, about 4 5 mm; distally, about 1.9 cm.

*Corolla*.—Quantity and arrangement: Five petals arranged in a single whorl; lower 59.5% portion of the petals are fused into a funnelform tube. Petal length: About 7.9 cm. Petal width: About 2.8 cm. Petal shape and appearance: Roughly unequal spatulate; slightly convex. Petal apex: Apiculate, unequal. Petal margin: Entire; moderately undulate. Petal texture and luster, upper surface: Smooth, glabrous; velvety; slightly glossy. Petal texture and luster, lower surface: Smooth, glabrous; slightly velvety; moderately glossy. Throat texture: Smooth, glabrous; velvety. Tube texture: Smooth, glabrous; slightly velvety. Color: Petal, when opening, upper surface: Close to N57B; towards the throat, close to N57C and N57D. Petal, when opening, lower surface: Close to 58B; central band, close to 63B; midvein, close to 63C. Petal, fully opened, upper surface: Close to N57C and N57D; venation, close to 63C; color does not change with subsequent development. Petal, fully opened, lower surface: Close to a blend of 59D and 63B; central band, close to 63C; midvein, close to 63D; color does not change with subsequent development. Throat: Close to 21A fading to close to 11C; at the base of the throat, close to 154D; venation, similar to lamina colors. Tube: Distally, close to N57D and proximally, close a blend of 11C and 11D; at the base, close to 151A slightly tinged with close to 173B; venation, similar to lamina colors.

*Sepals*.—Quantity and arrangement: Five sepals arranged in a single whorl. Length: About 8 mm. Width: About 1.75 mm. Shape: Lanceolate. Apex: Narrowly acuminate. Base: Broadly cuneate and fused. Margin: Entire. Texture and luster, upper surface: Smooth, glabrous; moderately glossy. Texture and luster, lower surface: Smooth, glabrous; slightly glossy. Color: When developing, upper surface: Close to 145B; towards the base, close to 145A; towards the margins and apex, close to 179A. When developing, lower surface: Close to 145C; towards the base, close to 145A; at the apex, close to 180C. Fully developed, upper surface: Close to 145D; towards the base, close to 145B; towards the margins and apex, close to 180A. Fully developed, lower surface: Close to a blend of 179A and 180A; towards the base, close to 145A.

*Peduncles*.—Length: About 6.5 cm. Diameter: About 2 mm. Strength: Strong. Aspect: About 30° from lateral branch axis. Texture and luster: Smooth, glabrous; moderately glossy. Color: Close to 143B to 143C.

*Pedicels*.—Length: About 1.2 cm. Diameter: About 2 mm. Strength: Strong. Aspect: About 10° to 50° from peduncle axis. Texture and luster: Smooth, glabrous; moderately glossy. Color: Close to 144B slightly to strongly tinged with close to 173A.

*Reproductive organs*.—Stamens: Quantity and arrangement: Typically five; basifixed; anthers connivent. Filament length: About 2 mm. Filament color: Close to 154D. Anther shape: Narrowly oblong. Anther size: About 1.75 mm by 9 mm. Anther color: Close to 161D. Pollen amount: None observed. Pistils: Quantity: Typically one. Pistil length: About 2.3 cm. Style length: About 2.1 cm. Style color: Close to 145C. Stigma diameter: About 1.75 mm. Stigma shape: Club-shaped, pointed. Stigma color: Close to 151A. Ovary color: Close to 143B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'LVDIP1807' as illustrated and described.

* * * * *